US00PP17084P2

(12) United States Plant Patent
Andrusiv

(10) Patent No.: US PP17,084 P2
(45) Date of Patent: Sep. 5, 2006

(54) ***BERBERIS* PLANT NAMED 'TINY GOLD'**

(50) Latin Name: *Berberis*
Varietal Denomination: Tiny Gold

(76) Inventor: Ing. Michal Andrusiv, J Metyse 1079, Litomysl (CS), 570 07

( * ) Notice: Subject to any disclaimer, the term of this patent is extended or adjusted under 35 U.S.C. 154(b) by 3 days.

(21) Appl. No.: 11/215,881

(22) Filed: Aug. 30, 2005

(51) Int. Cl.
*A01H 5/00* (2006.01)

(52) U.S. Cl. ..... Plt./241
(58) Field of Classification Search ..... Plt./241
See application file for complete search history.

(56) References Cited

PUBLICATIONS

Upov Plant Variety Database search for 'Tiny Gold'.*

* cited by examiner

*Primary Examiner*—Kent Bell
*Assistant Examiner*—Annette H Para

(57) ABSTRACT

A new cultivar of *Berberis* plant named 'Tiny Gold' that is characterized by a low spreading habit and bright yellow foliage. In combination these traits set 'Tiny Gold' apart from all other existing varieties of *Berberis* known to the inventor.

1 Drawing Sheet

Genus: *Berberis*. Species: *thunbergii*.
Denomination: Tiny Gold.

BACKGROUND OF THE INVENTION

The present invention relates to a new and distinct cultivar of barberry that is grown as a dwarf shrub for container or landscape. The new cultivar is known botanically as *Berberis thunbergii* and will be referred to hereinafter by the cultivar name 'Tiny Gold'.

'Tiny Gold' was selected by the inventor in Litomysl, The Czech Republic in 1994, for unique foliage color. The new cultivar 'Tiny Gold' is a hybrid plant that resulted from directed cross-pollination conducted by the inventor in a cultivated area of Litomysl, The Czech Republic. Cross-pollination was between an individual plant of seed parent *Berberis thunbergii* 'Aurea' (unpatented) and an individual plant of pollen parent *Berberis thunbergii* 'Atropurpurea Nana' (unpatented).

The new *Berberis* variety 'Tiny Gold' is a deciduous dwarf shrub characterized by bright yellow foliage. This foliage color continues throughout the summer season. There are no dwarf *Berberis*, known to the inventor, that exhibit this foliage color. The height of the plant is approximately half of the width. To date the inventor has observed no flowers produced by 'Tiny Gold'. The foliage color and plant habits distinguish 'Tiny Gold' from all other *Berberis* known to the inventor.

The new *Berberis* variety 'Tiny Gold' differs from the yellow foliage female parent plant *Berberis thunbergii* 'Aurea' in that 'Tiny Gold' is smaller in size, brighter yellow in color, and more compact. The new *Berberis* variety 'Tiny Gold' differs from the purple foliaged male parent plant *Berberis thunbergii* 'Atropurpurea Nana' in that 'Tiny Gold' is bright yellow in color whilst exhibiting similar dwarf habit.

The first asexual reproduction of 'Tiny Gold' was conducted by the inventor in a cultivated area of Litomysl, The Czech Republic. The method used for asexual propagation was vegetative cuttings. Since that time the distinguishing characteristics of 'Tiny Gold' have been determined stable and have reproduced true to type in successive generations of asexual reproduction.

An application for European Community Plant Variety Rights was filed Oct. 17, 2003, serial number 2003/1841. The first sale or distribution to the public of any plants of 'Tiny Gold' occurred on Sep. 2, 2004.

SUMMARY OF THE INVENTION

The following traits have been repeatedly observed and represent the characteristics of the new *Berberis* cultivar 'Tiny Gold'. These traits in combination distinguish 'Tiny Gold' from all other commercial varieties of *Berberis* known to the inventor. 'Tiny Gold' has not been tested under all possible conditions and phenotypic differences may be observed with variations in environmental, climatic and cultural conditions, without however, any variance in genotype.

1. *Berberis* 'Tiny Gold' is a deciduous shrub.
2. *Berberis* 'Tiny Gold' is suitable for use in containers or the landscape.
3. To date *Berberis* 'Tiny Gold' has not produced flowers.
4. *Berberis* 'Tiny Gold' exhibits a broad, low spreading habit.
5. *Berberis* 'Tiny Gold' exhibits bright yellow foliage.
6. *Berberis* 'Tiny Gold' is propagated using vegetative cuttings.
7. *Berberis* 'Tiny Gold' is hardy to USDA Zone 5.
8. *Berberis* 'Tiny Gold' achieves after 2 years 27 cm. in width and 14 cm. in height in a 2-liter container.

BRIEF DESCRIPTION OF THE DRAWINGS

The accompanying color drawing.

BOTANICAL DESCRIPTION OF THE PLANT

Figure 1:
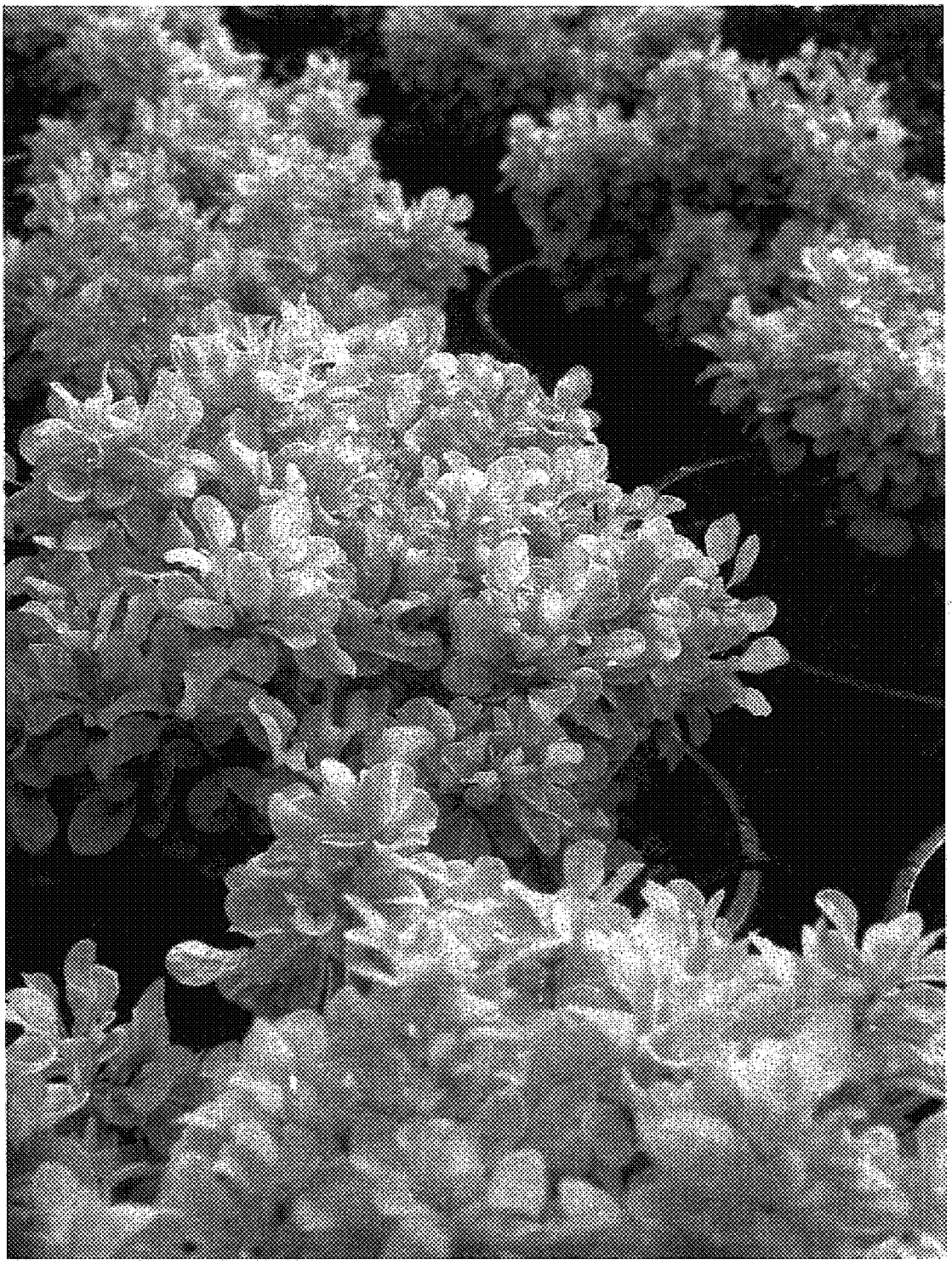
FIG. 1, illustrates the overall appearance of the new cultivar 'Tiny Gold' showing the colors as true as it is reasonably possible to obtain in colored reproductions of this type. The drawing was made in September. The plants shown on the drawing are 2-years-old in 2 liter containers, and were grown out-of-doors in Boskoop, The Netherlands. The drawing illustrates the bright yellow foliage and spreading of 'Tiny Gold'. Daytime temperatures averaged 15° Centigrade to 30° Centigrade. Nighttime temperatures ranged from 7° Centigrade to 14° Centigrade. The light was normal outdoor light level. No photoperiodic treatments and no growth retardants were applied to the plants. Colors in the drawings may differ from the color values cited in the detailed botanical description, which accurately describe the actual colors of the new variety of *Berberis* named 'Tiny Gold'. Drawings were made using conventional techniques and although colors may appear different from actual colors due to light reflectance they are as accurate as possible by conventional photography.

The following is a detailed description of 'Tiny Gold' as grown in a 2-liter containers, out-of-doors in Boskoop, The Netherlands. The color determinations are in accordance with the 2001 Royal Horticultural Society Colour Chart except where general color terms of ordinary dictionary significance are used. The growing requirements are similar to the species.

Botanical classification: Genus: *Berberis*. Species: *thunbergii*.
Denomination: 'Tiny Gold'.
Commercial classification: Deciduous shrub.
Use: Plant for use in containers or landscape.
Common name: Barberry.
Commercial container size: For liner production, a 5 cm round or square plug or cell or container; for planting in the garden or landscape, a 1 gallon or equivalent or larger container.
Cultural requirements: Plant in full sun to light shade in well-drained soil with moderate to regular water.
Parentage: *Berberis* 'Tiny Gold' is a hybrid plant that resulted from cross-pollination of the following parents:
- *Seed parent.*—*Berberis thunbergii* 'Aurea'.
- *Pollen parent.*—*Berberis thunbergii* 'Atropurpurea Nana'.

Plant description:
- *Bloom period.*—None. Plant has not bloomed to date.
- *Plant habit.*—Broad spreading habit.
- *Overall plant shape.*—Flattened globular.
- *Vigor.*—Low vigor.
- *Root system.*—Fibrous roots.
- *Plant dimensions.*—27 cm. in width and 14 cm. in height in a 2-liter container.
- *Growth rate.*—An average of 6 cm. per season until mature.
- *Hardiness.*—USDA Zone 5.
- *Propagation.*—Propagation is accomplished using stem tip or internodal cuttings.
- *Rooting time.*—An average of 6 weeks is needed for an initial cutting to develop roots.
- *Crop time.*—24 months are needed to produce a commercial 2-liter container from a rooted cutting.
- *Special growing considerations.*—Pinching back improves branching.
- *Disease resistance and susceptibility.*—Not more susceptible to pest and diseases than other *Berberis thunbergii* cultivars known to the inventor. USDA-ARS, Cereal Disease Laboratory completed testing and found the cultivar resistant to Wheat Stem Rust.

Stem:
- *Stem color* (*immature stems*).—Ranges from 32A to 32C.
- *Stem color* (*mature stems*).—Color ranges from 166A to 200B.
- *Stem surface.*—Smooth, slightly glossy.
- *Internode length.*—6 mm between nodes.
- *Branching habit.*—Basal branching with free branching lateral stems.
- *Number of lateral branches.*—An average of 8 lateral branches.
- *Lateral branch length.*—An average of 7–8 cm. in length.
- *Lateral branch diameter.*—An average of 2 mm. in diameter.
- *Internode length.*—An average of 6 mm. between nodes.
- *Stem shape.*—Cylindrical.
- *Stem surface.*—Mature stems are slightly ribbed while immature stems are glabrous and glossy.
- *Stem strength.*—Moderate in strength.
- *Stem pubescence.*—None present.
- *Stipules, tendrils, thorns or spines.*—Thorns present.
- *Thorn length.*—Thorns range in length from 4–6 mm.
- *Thorn apex.*—Acuminate.
- *Thorn surface.*—Glabrous.
- *Thorn base.*—Truncate.
- *Thorn color.*—Individual colors N167A and N199B are both present on an individual plant.

Foliage:
- *Type.*—Deciduous.
- *Arrangement.*—Alternate.
- *Durability of leaf to stress.*—Moderate to high.
- *Shape.*—Obovate.
- *Margins.*—Entire; wavy.
- *Division.*—Simple.
- *Apex.*—Individual leaf apices range from mucronulate to abruptly acute.
- *Base.*—Elongated attenuate.
- *Pubescence* (*adaxial and abaxial surfaces*).—None present.
- *Leaf surface* (*abaxial and adaxial surfaces*).—Glabrous.
- *Leaf appearance* (*adaxial and abaxial surfaces*).—Slightly glossy.
- *Quantity of leaves per lateral branch.*—An average of 65 leaves per lateral branch.
- *Leaf length.*—Individual leaves are an average of 2.1 cm. in length.
- *Leaf width.*—Individual leaves are an average of 1.7 cm. in width.
- *Leaf attachment.*—Sessile.
- *Leaf color* (*adaxial surface*).—13B changing to 138A.
- *Leaf color* (*abaxial surface*).—13C changing to 138 A to B.
- *Venation.*—Pinnate.
- *Vein color on adaxial surface* (*immature leaf*).—13B changing to 138A.
- *Vein color on abaxial surface* (*immature leaf*).—13C changing to 138 A to B.
- *Fragrance.*—None.

Flowers, reproductive organs and seed: 'Tiny Gold' has not flowered to date.

What is claimed is:

1. A new and distinct cultivar of *Berberis* plant named 'Tiny Gold', as described and illustrated herein.

* * * * *